(12) United States Patent
Neander et al.

(10) Patent No.: US 9,857,285 B2
(45) Date of Patent: Jan. 2, 2018

(54) ENVIRONMENTAL SENSOR AND METHOD OF OPERATING THE SAME

(71) Applicant: Venturedyne, Ltd., Pewaukee, WI (US)

(72) Inventors: Nicholas C. Neander, Angelus Oaks, CA (US); David L. Chandler, Highland, CA (US)

(73) Assignee: Venturedyne, Ltd., Pewaukee, WI (US)

( * ) Notice: Subject to any disclaimer, the term of this patent is extended or adjusted under 35 U.S.C. 154(b) by 122 days.

(21) Appl. No.: 14/972,866

(22) Filed: Dec. 17, 2015

(65) Prior Publication Data

US 2017/0176316 A1 Jun. 22, 2017

(51) Int. Cl.
*G05B 1/02* (2006.01)
*G01N 15/14* (2006.01)

(52) U.S. Cl.
CPC . *G01N 15/1404* (2013.01); *G01N 2015/1409* (2013.01)

(58) Field of Classification Search
CPC ...... H02P 7/00; H02K 11/21; G01N 15/0266; G01N 15/1227
See application file for complete search history.

(56) References Cited

U.S. PATENT DOCUMENTS

| | | |
|---|---|---|
| 3,343,402 A | 9/1967 | Hubner |
| 3,375,700 A | 4/1968 | Hubner |
| 3,450,333 A | 6/1969 | Nihot et al. |
| 4,047,912 A | 9/1977 | Markland |
| 4,588,351 A | 5/1986 | Miller |
| 4,746,215 A | 5/1988 | Gross |
| 5,187,419 A | 2/1993 | DeLange |
| 5,332,512 A | 7/1994 | Wells |
| 5,825,487 A | 10/1998 | Felbinger et al. |
| 6,024,491 A | 2/2000 | Bak |
| 6,031,610 A | 2/2000 | Adams |
| 6,091,494 A | 7/2000 | Kreikebaum |

(Continued)

OTHER PUBLICATIONS

International Search Report and Written Opinion for Application No. PCT/US2016/067087 dated Apr. 13, 2017 (13 pages).

(Continued)

*Primary Examiner* — Karen Masih
(74) *Attorney, Agent, or Firm* — Michael Best & Friedrich LLP

(57) ABSTRACT

A gaseous-fluid environmental sensor having a gaseous-fluid flow system that defines a flow path coupling an intake port to an exhaust port. The gaseous-fluid flow system includes a blower and a flow sensor. The blower includes a motor and the flow sensor senses a flow-related parameter. The gaseous-fluid environmental sensor further includes a battery, an electrical sensor sensing an electrical power-related parameter, and a controller electrically coupled to the electrical sensor, the flow sensor, and the motor. The controller is configured to generate a composite drive waveform having a first component based on the sensed flow-related parameter and a second component based on the sensed electrical power-related parameter. The controller is further configured to drive the motor using the composite drive waveform. Also disclosed is a method of controlling the gaseous-fluid environmental sensor.

17 Claims, 16 Drawing Sheets

(56) References Cited

U.S. PATENT DOCUMENTS

| | | |
|---|---|---|
| 6,099,608 A | 8/2000 | Harms et al. |
| 6,167,107 A | 12/2000 | Bates |
| 6,277,176 B1 | 8/2001 | Tang et al. |
| 6,408,704 B1 | 6/2002 | Willeke |
| 6,517,612 B1 | 2/2003 | Crouch et al. |
| 6,706,243 B1 | 3/2004 | Sias et al. |
| 6,821,310 B2 | 11/2004 | Hedstrom |
| 6,887,710 B2 | 5/2005 | Call et al. |
| 6,951,147 B2 | 10/2005 | Call et al. |
| 6,997,686 B2 | 2/2006 | Agrawal et al. |
| 7,063,519 B2 | 6/2006 | Agrawal et al. |
| 7,201,036 B2 | 4/2007 | Custer et al. |
| 7,211,915 B2 | 5/2007 | Conrady et al. |
| 7,347,112 B2 | 3/2008 | Kay |
| 7,439,855 B1 | 10/2008 | Yufa |
| 7,535,150 B1 | 5/2009 | Wilson |
| 7,724,150 B2 | 5/2010 | Chandler et al. |
| 7,733,486 B2 | 6/2010 | Imre |
| 7,796,255 B2 | 9/2010 | Miller |
| 7,895,000 B2 | 2/2011 | Chandler et al. |
| 8,147,302 B2 | 4/2012 | Desrochers et al. |
| 8,408,046 B2 | 4/2013 | Xu et al. |
| 8,505,395 B2 | 8/2013 | Graze, Jr. |
| 8,584,509 B2 | 11/2013 | Groves |
| 8,706,320 B2 | 4/2014 | Kelm |
| 8,800,383 B2 | 8/2014 | Bates |
| 8,899,946 B2 | 12/2014 | Teshima et al. |
| 2001/0043652 A1 | 11/2001 | Hooley |
| 2005/0158172 A1 | 7/2005 | Snyder et al. |
| 2006/0065752 A1 | 3/2006 | Poirier |
| 2006/0263925 A1 | 11/2006 | Chandler |
| 2007/0113686 A1 | 5/2007 | Desrochers et al. |
| 2007/0297922 A1 | 12/2007 | Kanai et al. |
| 2008/0226472 A1 | 9/2008 | Kanai et al. |
| 2008/0229805 A1 | 9/2008 | Barket et al. |
| 2009/0237659 A1* | 9/2009 | Miers ............... G01N 15/1459 356/338 |
| 2010/0045215 A1 | 2/2010 | Hawker et al. |
| 2011/0197571 A1 | 8/2011 | Visser |
| 2012/0199129 A1 | 8/2012 | Kenyon et al. |
| 2013/0239660 A1 | 9/2013 | Gunderson et al. |
| 2014/0174154 A1 | 6/2014 | Marra et al. |
| 2014/0219834 A1 | 8/2014 | Tamaoka et al. |

OTHER PUBLICATIONS

TSI® AEROTRAK® With Pump Particle Counters Installation Considerations, TSI Incorporated <www.tsi.com> CC-110 dated Apr. 30, 2014 (8 pages).

High Efficiency Air Bearing Turbo Blower, APG-Neuros <info@apg-neuros.com>, available Mar. 27, 2015 (12 pages).

Office Action from the U.S. Patent and Trademark Office for U.S. Appl. No. 14/972,884 dated Jul. 21, 2017 (20 pages).

\* cited by examiner

Prior art

ENVIRONMENTAL SENSOR AND METHOD OF OPERATING THE SAME

BACKGROUND

The invention relates to environmental sensors, such as particle counters that are used to detect particles in air or liquid environments.

Environmental sensors move a fluid past a sensor for sensing an aspect of the fluid. The environmental sensor may also filter the fluid. For example, particle counters can be used to detect microscopic particles in gaseous fluids. Particle counters can be used, for example, to monitor clean environments and process gaseous fluids where contamination of a product being manufactured can render that product unsuitable for its intended purpose. Particle counters can include means of moving a measured and controlled volume of air through the sensor, a light source, collection optics, photo detector, circuitry for converting detected scattered light to electrical signals, a means of discriminating electrical signals caused by particles at the sizes of interest, and a means of counting the number of times that those signals occur over some period of time.

Pharmaceutical manufacturers maintain controlled environments that meet cleanliness standards for the maximum number of particles greater than a certain size occupying a specified volume of air. Environments where pharmaceutical products are formulated and packaged are regulated by government agencies to insure compliance to the cleanliness standards.

Semiconductor and aerospace manufacturers also monitor the cleanliness of their process fluids, gases, and environments in order to eliminate sources of contamination and increase yield. Other industries, for example those that make automotive products, micro-machined structures, and optical assemblies also monitor their environments to detect and control contamination that affects product performance and quality.

Particle counters commonly are battery powered. Exemplary battery powered particle counters using a centrifugal blower include U.S. Pat. Nos. 5,515,164; 5,600,438; RE37,353; 5,825,487; and 7,752,930 and using a regenerative centrifugal blower include U.S. Pat. No. 6,167,107, all of which are incorporated herein by reference. One or more of the patents also disclose methods and systems for incorporating blowers with the associated methods for measuring and controlling the flow rate through the sensor.

Older particle counters include positive displacement pumps with diaphragms or carbon vanes. These counters require considerably more power which made battery operation impractical for most applications that require the common flow rate of 1 CFM (cubic foot per minute). However, the use of the centrifugal blower alleviated this problem and in the years that followed, battery powered flow rates were able to increase up to 100 LPM (liters per minute), which is almost four time greater than 1 CFM. Advances in battery technology have also enabled these higher flow rate particle counters. However, the blowers used in particle counters have not advanced since the above-referenced patents were issued.

Accordingly, there is the need for a new and useful environmental sensor with an improved blower and related control.

SUMMARY

In one embodiment, the invention provides a gaseous-fluid environmental sensor having a gaseous-fluid flow system that defines a flow path coupling an intake port to an exhaust port. The gaseous-fluid flow system includes a blower and a flow sensor. The blower includes a motor and the flow sensor senses a flow-related parameter. The gaseous-fluid environmental sensor further includes a battery, an electrical sensor sensing an electrical power-related parameter, and a controller electrically coupled to the electrical sensor, the flow sensor, and the motor. The controller is configured to generate a composite drive waveform having a first component based on the sensed flow-related parameter and a second component based on the sensed electrical power-related parameter. The controller is further configured to drive the motor using the composite drive waveform.

The electrical power-related parameter may include a sensed battery voltage or a sensed motor voltage. The sensed flow-related parameter may include a sensed mass of gaseous fluid flow through the gaseous-fluid environmental sensor.

In another embodiment, the invention provides a method of controlling a gaseous-fluid environmental sensor. The method includes creating a flow of fluid from a space through the gaseous-fluid environmental sensor, determining a flow-related parameter of the flow of fluid, determining an electrical power-related parameter of the gaseous-fluid environmental sensor, generating a first component of a composite drive waveform based on the determined flow-related parameter, generating a second component of the composite drive waveform based on the determined electrical power-related parameter, and driving a motor with the composite drive waveform.

Other aspects of the invention will become apparent by consideration of the detailed description and accompanying drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting.

Although directional references, such as upper, lower, downward, upward, rearward, bottom, front, rear, etc., may be made herein in describing the drawings, these references are made relative to the drawings (as normally viewed) for convenience. These directions are not intended to be taken literally. In addition, terms such as "first", "second", and "third" are used herein for purposes of description and are not intended to indicate or imply relative importance or significance.

Figure 1:
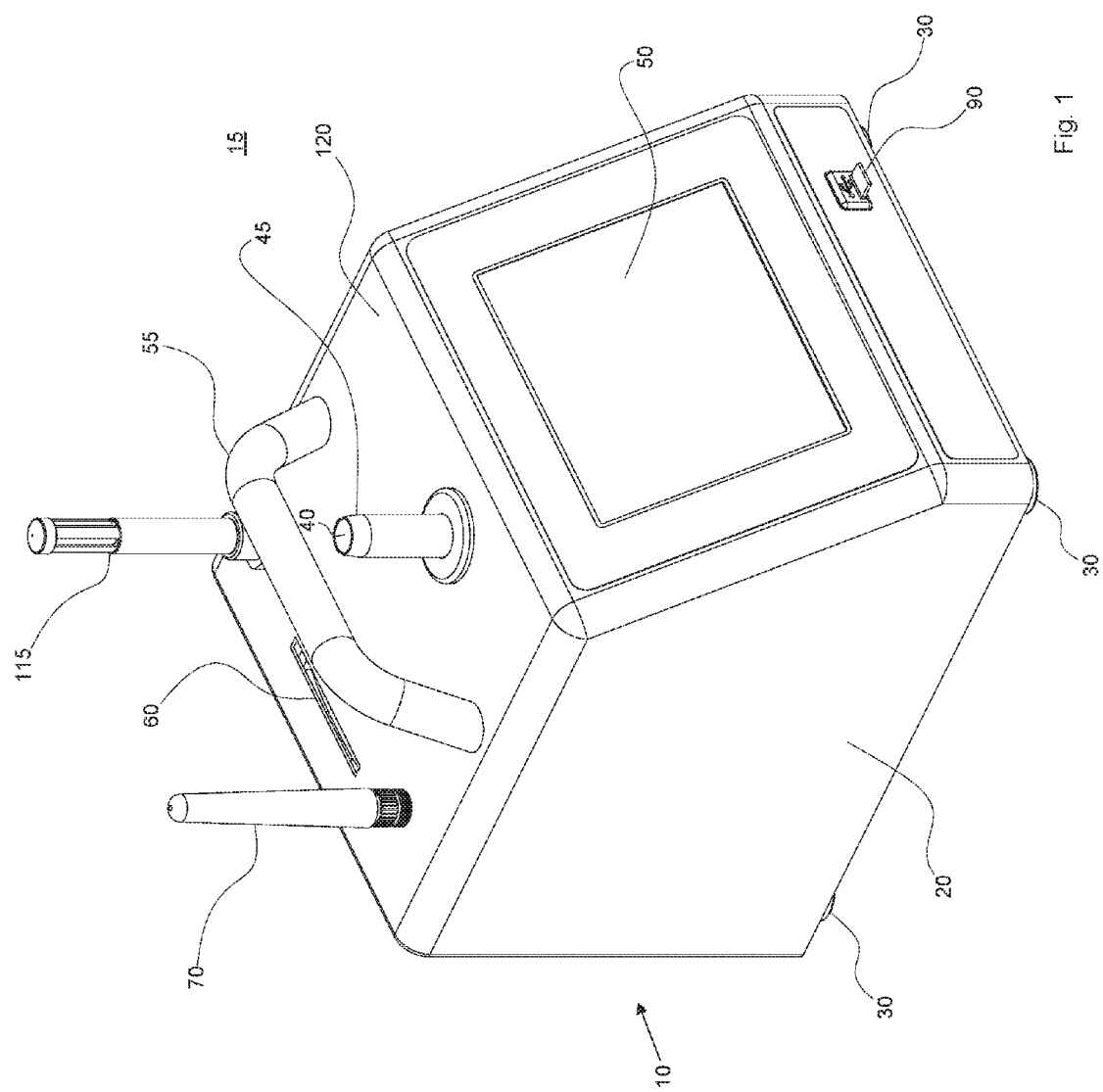
FIG. 1 is a perspective view of a portable gaseous-fluid particle counter from a first vantage point.
Figure 2:
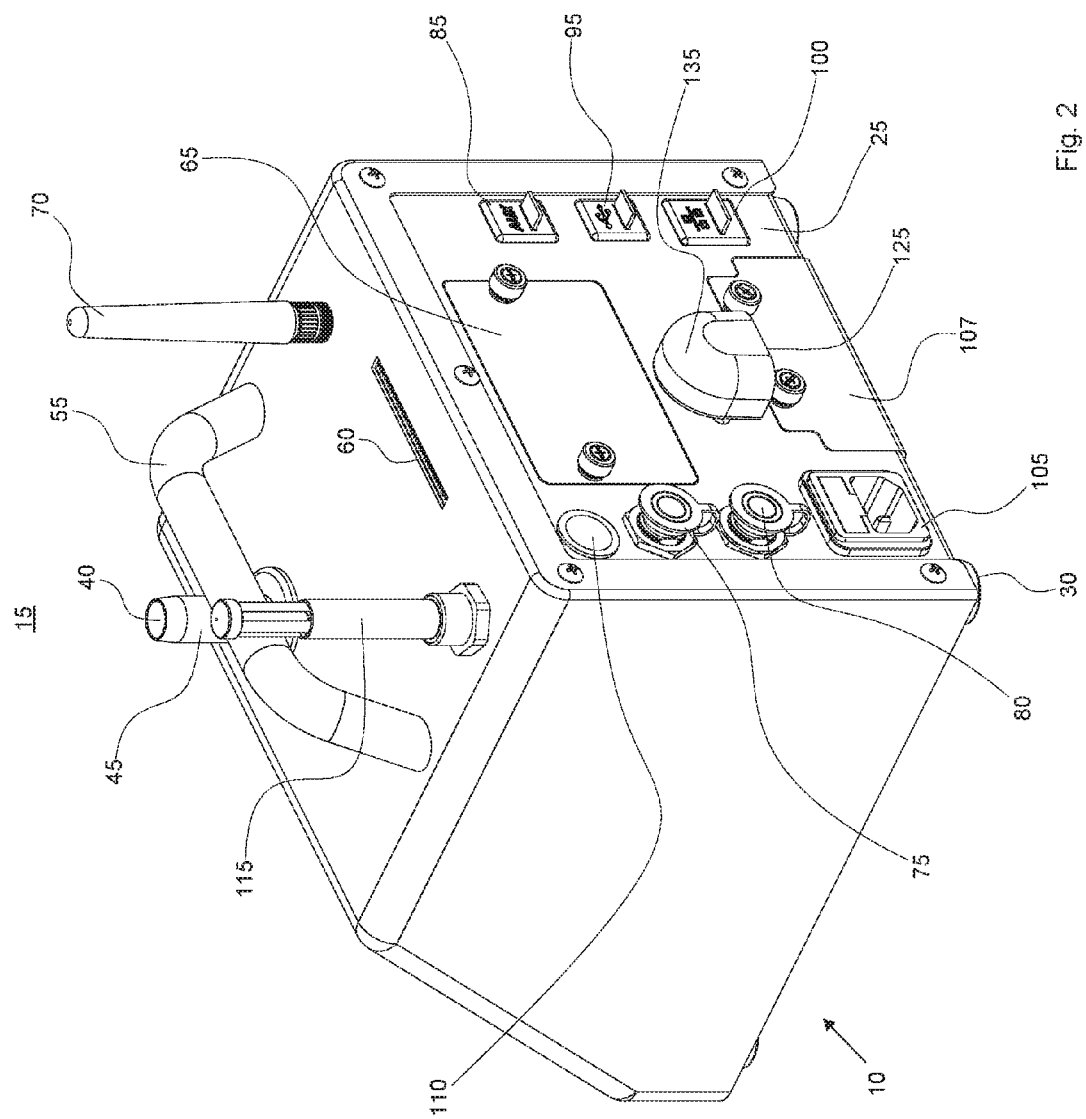
FIG. 2 is a perspective view of the particle counter of FIG. 1 from a second vantage point.

FIGS. 1 and 2 illustrate an environmental sensor. The shown environmental sensor is a portable gaseous-fluid particle counter 10 for counting and collecting microbial particles from a gaseous fluid of an environment 15. It is to be understood that microbial particles can include biologically active particles such as bacteria, fungi, and similar particles. Moreover, the term gaseous fluid makes reference to ambient air and other gaseous fluid that may not be considered as ambient air, such as, but not limited to, air in a clean room environment. While the particle counter 10 is shown throughout the figures, aspects of the invention can be used in other environmental sensors, which may also encompass environmental filters. The particle counter 10 shown in the figures is an exemplary construction and it is to be understood that other physical appearances fall within the scope of the invention.

With reference to FIGS. 1-2, the particle counter 10 includes a support structure, such as a housing, which may be divided into a top enclosure 20 and a bottom enclosure 25. However, the support structure does not need to be solely the housing. Rather, the support structure can include additional structure for supporting the gaseous-fluid flow system (discussed below), which is then enclosed by the housing. The particle counter 10 also includes a set of supports 30. The supports 30 help the particle counter 10 sit in a first orientation, which is shown in FIGS. 1-2, defining a gaseous fluid intake port 40 facing upward. The just-described orientation is relative to the position of the particle counter 10 within the FIGS. 1 and 2. It is to be understood that the intake port 40 may be at other orientations.

The gaseous fluid intake port 40 is formed by an inlet structure, which is shown as an inlet tube 45. However, other environmental sensors and particle counters may use other inlet structures to receive a fluid depending on the type of fluid being acquired. Other inlet structures are shown in, for example, the above referenced patents.

The particle counter 10 also includes a user interface for a user to operate the particle counter 10 and/or to view information related to the particle counter 10 and the samples collected by the particle counter 10. The user interface is shown as a display 50 and a power/reset button 110. The user can view information provided by the particle counter 10 via the display and control the operation of the particle counter 10 via the power/reset button 110. Other constructions of the particle counter 10 can include different types of user interfaces, such as touch displays, liquid crystal displays, light emitting diodes, incandescent lights, keypads or keyboards, buttons, switches, pointing devices, touch pads, etc.

In the construction shown, the particle counter 10 includes a handle 55 mounted to the top enclosure 20. The handle 55 allows a user to transport the particle counter 10 between different locations; i.e., the shown particle counter 10 is portable. Also shown are a printer slot 60 and a printer door 65. A printer is housed in the particle counter 10, receives paper by way of the printer door 65, and dispenses printed paper through the printer slot 60.

The particle counter 10 can wirelessly communicate with one or more remote devices via a wireless antenna 70 or can communicate via wired connections. Exemplary wired connections shown include input/output connectors 75 and 80, an RJ-11 auxiliary connector 85, a USB type A connector 90, a USB type B connector 95, and an Ethernet connector 100. While various connector types and protocol types are mentioned, these types are only exemplary.

The particle counter 10 shown also includes a port 105 to receive a power cord, a battery door 107, a power/reset button 110, and a room humidity and temperature sensor 115.

The intake port 40 shown in FIGS. 1-2 is located on a top panel 120 of the top enclosure 20. An exhaust port 125 of an outlet structure exhausts gaseous fluid external to the particle counter 10. The exhaust port 125 is shown in FIG. 2 as being on a side panel 130 of the bottom enclosure 25 and the outlet structure includes an outlet tube 135 in the shape of a shroud for deflecting the gaseous fluid.

With reference to FIGS. 3 through 7, the particle counter 10 includes a support platform 140 for supporting the internal components (e.g., a control system and a gaseous-fluid flow system) of the particle counter 10. The gaseous-fluid flow system includes the inlet structure (i.e., the inlet tube 45), a particle count sensor 145, a flow connect block 150, a sensor/blower mounting plate 155, a blower 160, a filter 165, a flow shunt 170, a flow sensor 175, the outlet structure (e.g., the outlet tube 135), and conduit (discussed below). The gaseous-fluid flow system is shown in FIGS. 3 through 6 as having a particular order. However, the order of the elements may change with different constructions. For a simple example, the filter 165 may be placed after the flow shunt 170. Other arrangements will be discussed below, but all the different permutations will not be discussed herein. The control system includes a DC power source (e.g., a battery) 180, a power supply 185, a motor sensor 190, the particle count sensor 145, the flow sensor 175, a controller 195, drive circuit 200, motor 205, and communication input/output interface 210. The control system can include other control elements not shown in FIG. 7, such as the user interface (e.g., display 50), other sensors (e.g., room humidity/temperature sensor 115), and the printer.

Referring again to FIGS. 3 through 7, the blower 160 is driven by a motor 205 to move gaseous-fluid through the particle counter 10. The blower is fluidly connected to the intake port 40 and is also fluidly connected to the exhaust port 125. The blower draws gaseous fluid from the environment 15 into the intake port 40 and through the particle count sensor 145 for counting particles. From the particle count sensor 145, the blower 160 continues to draw the gaseous fluid through the flow connect block 150 and the sensor/blower mounting plate 155, and into the blower 160. The blower 160 then pushes the gaseous fluid to the filter 165. Particles in the gaseous fluid are filtered by the filter 165 depending on the type of filter used. After being pushed through the filter 165, the gaseous fluid enters the flow shunt 170. The flow shunt 170 includes a fluid restrictor 215 (best shown in FIG. 4) that shunts a small amount of gaseous fluid for flow sensing. A conduit 220 provides a channel for the shunted fluid toward the flow sensor 175. The flow sensor 175 senses a parameter relating to the flow of the gaseous fluid through the flow path based on the shunted fluid. The shunted fluid returns to the flow shunt 170 via conduit 225. The returned gaseous fluid recombines with the main gaseous fluid flow and exhausts from the exhaust port 125.

The particle count sensor 145 is configured to detect particles within a predetermined size range. The shown particle count sensor 145 is an aerosol particle counter that operates under the principle of light scattering detection. However, other aerosol particle counters (e.g., a particle counter that operates under the principle of light obscuration) and other particle counters can be used depending on the type of environment. The flow enters the particle count sensor 145 through a sensor intake port 230 and exits through a sensor exhaust port 235.

During one operation of the particle count sensor 145, particles are detected by light scattering. More specifically, a light source generates a laser beam within a particle detection portion of the particle count sensor 145. Particles flow through the particle detection portion and through the laser beam. The particles traversing the particle detection portion result in light scattering, which is detected by an optical detector. The optical detector generates a voltage pulse as a result of detecting the light scattering and sends the voltage pulse to a sensor controller of the particle count sensor 145. The sensor controller is operable to determine information regarding the particles (e.g., particle size, velocity, composition) based on the voltage pulse generated by the optical detector. The information determined by the sensor controller can be saved in memory and/or sent to the controller 195. It is envisioned that the sensor controller can be combined with the controller 195 such that the voltage pulse is provided to the controller 195.

Environmental sensors, like the particle counter 10, may use centrifugal blowers or regenerative blowers. These types of blowers commonly include a brushless DC (BLDC) motor. A BLDC motor includes a rotor on to which an impeller is attached. The rotor includes a permanent magnet. A BLDC motor also includes a stator, which consists of electromagnetic coils that are energized. The energized coils produce a magnetic field that interacts with a magnetic field of the rotor. An electronic control system senses the angular position of the rotor and energizes the electromagnetic coils in the proper phase relative to the rotor to make it rotate.

Existing environmental sensors may suffer inefficiency in the air moving system when a conventional blower with lubricated ball bearings is used. Example reasons for the inefficiency include: 1) the blower motor wastes energy overcoming the centrifugal force of the impeller, 2) a reduction of the mass of the impeller reduces energy spent overcoming centrifugal force inertia at the expense of a higher speed being required to move the same volume of air across the same differential pressure, 3) the lifetime of the blower is reduced when it is run at a higher speed due to ball bearing failure caused by the breakdown of the lubricant in the bearings, 4) the ball bearings and lubricant present a second source of drag which wastes energy, and 5) the low viscosity lubricants used in high speed motors may be expelled from the bearings during normal use. Microscopic droplets of lubricant can be a source of contamination in a cleanroom. The motor and blower housing should be sealed to alleviate this problem.

In alternative, the example blower 160 shown in the particle counter 10 is a model TFO37 micro blower available from Copal Electronics. The blower 160, and more specifically the motor, includes a non-contact fluid dynamic bearing. The non-contact fluid dynamic bearing may also be referred to as an air bearing, hydrodynamic bearing, or aero-dynamic bearing. The air enters the impeller along the rotating axis through a blower intake port 240 and exits through a blower exhaust port 245.

Figure 8:
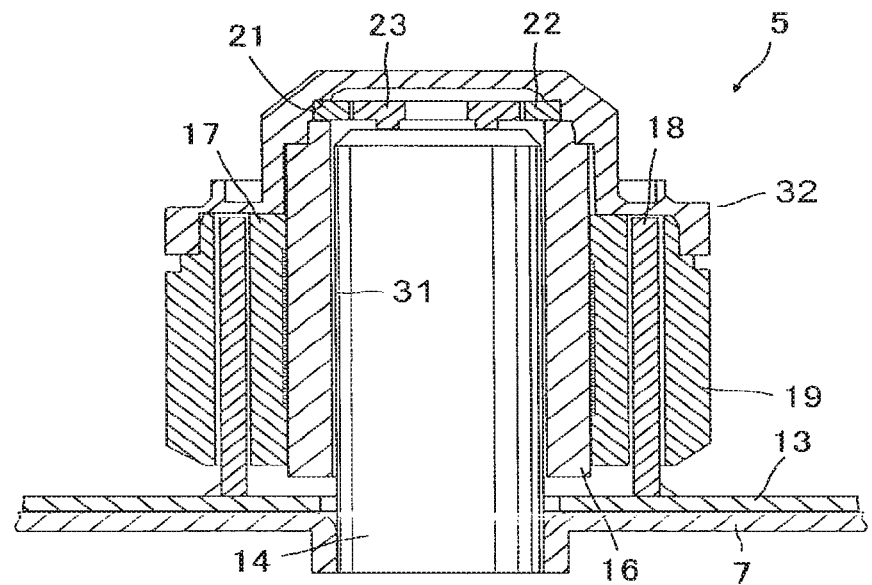
FIG. 8 is a sectional view of a motor capable of being used with the blower according to one embodiment.
Figure 9:
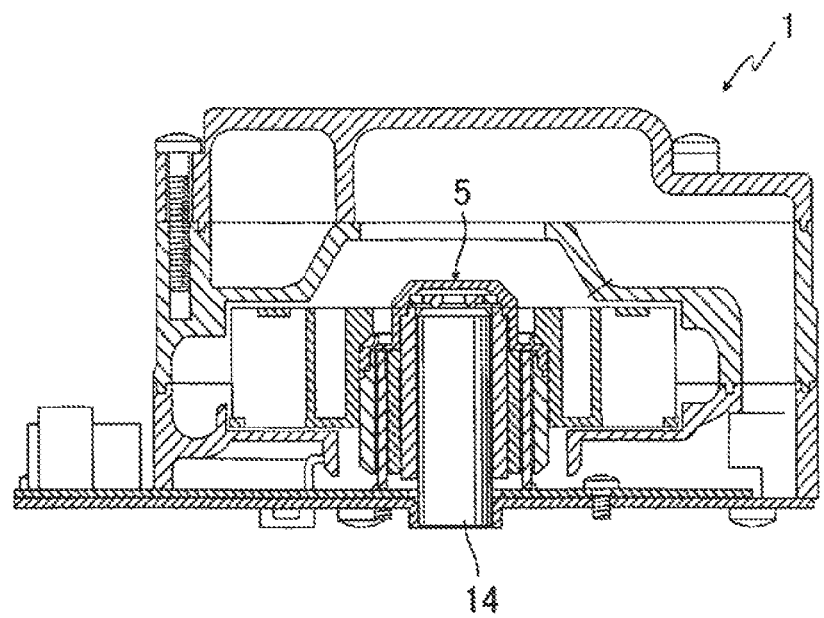
FIG. 9 is a sectional view of a blower capable of being used in the particle counter of FIG. 1.

Further description for various constructions of a blower having a fluid dynamic bearing is disclosed in U.S. Pat. No. 7,628,582, which is incorporated herein by reference. FIGS. 8 and 9, which are from U.S. Pat. No. 7,628,582, show a BLDC motor 5 and blower 1 capable of being used with the blower 160. The motor 5 is further comprised of a circuit board 13 fixed to a surface of the blower housing. The circuit board 13 can include the drive circuit 200 (FIG. 7) for the motor 5. A fixed shaft 14 projects upward from the circuit board 13. A sleeve 16 is positioned at an outer circumferential part of the shaft 14 via a space 31. A rotor 17 is positioned at an outer circumferential part of the sleeve 16. A stator with a commutation coil 18 is attached to the circuit board 13 so as to be positioned at an outer circumferential part of the rotor 17. A back yoke 19 is provided so as to position at an outer circumferential part of the coil 18. A thrust magnet 22, which is formed in the shape of a ring, is fixed to a concave part 21, which is formed at the upper part of the hub 32 which covers the shaft 14. The thrust magnet 22 supports the sleeve 16, rotor 17, and back yoke 19. The hub 32 acts as the rotation member which covers an upper part of the shaft 14 and the outer circumferential part of the back yoke 19. A thrust magnet 23 is fixed to the upper part of the shaft 14 so as to face to the thrust magnet 22. The impeller 6 can be attached to the hub 32. U.S. Pat. No. 7,628,582 can be referred to for further discussion relating to a non-contact fluid dynamic bearing.

A fluid dynamic bearing is a bearing that allows rotation without the physical contact between bearing surfaces or the presence of a lubricant as is required with bushing, roller, or ball type bearings. This eliminates a potential source of contamination to a cleanroom environment. The fluid bearing does not use a lubricant, has substantially no drag, and enables the motor to rotate at high RPM's reliably without suffering bearing failure.

Fluid dynamic bearings are bearings that use a thin film of pressurized air to provide an exceedingly low friction load-bearing interface between surfaces. The fluid film of the bearing is air that flows through the bearing itself to the bearing surface. The design of the air bearing is such that, although the air constantly escapes from the bearing gap, the pressure between the faces of the bearing keeps the surfaces from contacting. A fluid dynamic bearing establishes the air cushion through its movement.

The motor 205, through the use of the fluid dynamic bearing, operates at a high RPM. In some constructions, the definition of high RPM is in a range of 20,000 RPM to 40,000 RPM. In more preferred constructions, the range is between 20,000 and 30,000 RPM, or even more preferred range is between 25,000 and 30,000 RPM.

Since the motor 205 can operate at a higher RPM, the mass of the impeller can be reduced which reduces energy spent overcoming centrifugal force inertia. The weight of the rotor/impeller assembly is light enough to provide the efficiency that establishes the basis for the high efficiency drive design. By way of example, the mass of the rotor/impeller assembly is approximately 31 grams for the TFO37 micro blower referenced earlier. In some constructions, the rotor/impeller assembly has a mass between 25-45 grams, with a more preferred mass between 25-35 grams. Also, the higher RPM allows for a smaller diameter impeller to provide the flow at the pressure required. For example, the diameter of the TFO37 micro blower is 3.7 cm. In some constructions the diameter of the impeller is between 3.0 cm and 4.5 cm, with a more preferred diameter between 3.5 cm and 4.0 cm. The TFO37 micro blower also has a small form factor with the volume occupied by the blower being less than 6.2 cu.in. In some constructions the occupied volume of the blower is between 5 cu.in. and 8 cu.in., with a more preferred volume between 5.5 cu.in. and 6.5 cu.in.

However, some constructions of the blower 160 require ventilation. Gaseous fluid from this ventilation should be evacuated to a space where heat and/or pressure will be removed from the space around the motor 205. For the blower 160 shown in the figures, a blower vent port 250 is used for this ventilation. Depending on the operation of the blower 160 (e.g., the blower 160 is accelerating versus decelerating) the gaseous fluid may be drawn into or exhausted from the blower vent port 250.

Referring again to FIGS. 3 through 6, the flow connect block 150 provides a means for connecting the blower vent port 250 from the blower 160 to a channel in the discharge path from the particle count sensor 145. Thus, the gaseous fluid used for venting the motor is not discharged to ambient air. In other words, the blower 160 is sealed to prevent leakage that would introduce errors in the flow communication.

The flow rate into the intake port 40 is controlled by a closed loop system that is in flow communication with the flow sensor 175. If the ventilation of the blower 160 is exhausted from the blower vent port 250 to ambient air, the ventilation will introduce errors since the sensed flow is not equal to the intake flow. The flow connect block 150 provides a means for connecting the blower vent port 250 from the blower 160 so as to recombine the ventilation air with the sample air to maintain accurate flow communication over the flow path.

Further, the exhaust port 125 of the particle counter 10 is exhausted into a controlled environment from which contaminants have been removed by filtration. The exhaust of the blower 160 must be filtered before it is exhausted into the controlled environment. The blower 160 is capable of overcoming the additional pressure drop of the filter 165 through which all sample air passes before being exhausted into the controlled environment. The blower 160 is sealed with the flow connect block 150 to prevent leakage that would allow unfiltered air to escape into the controlled environment.

Figure 3:
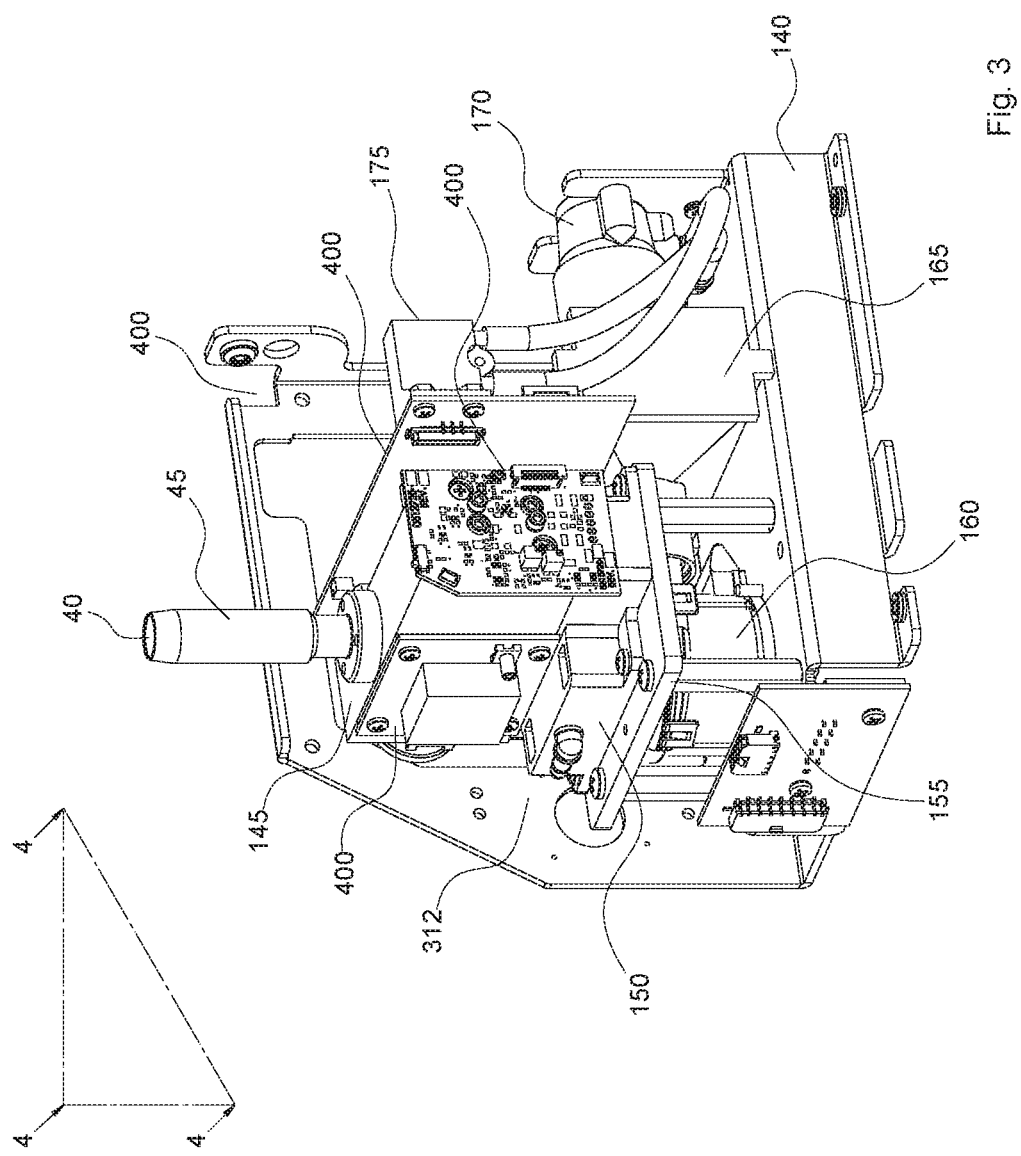
FIG. 3 is a perspective view of an internal portion of the particle counter of FIG. 1 from a third vantage point.
Figure 4:
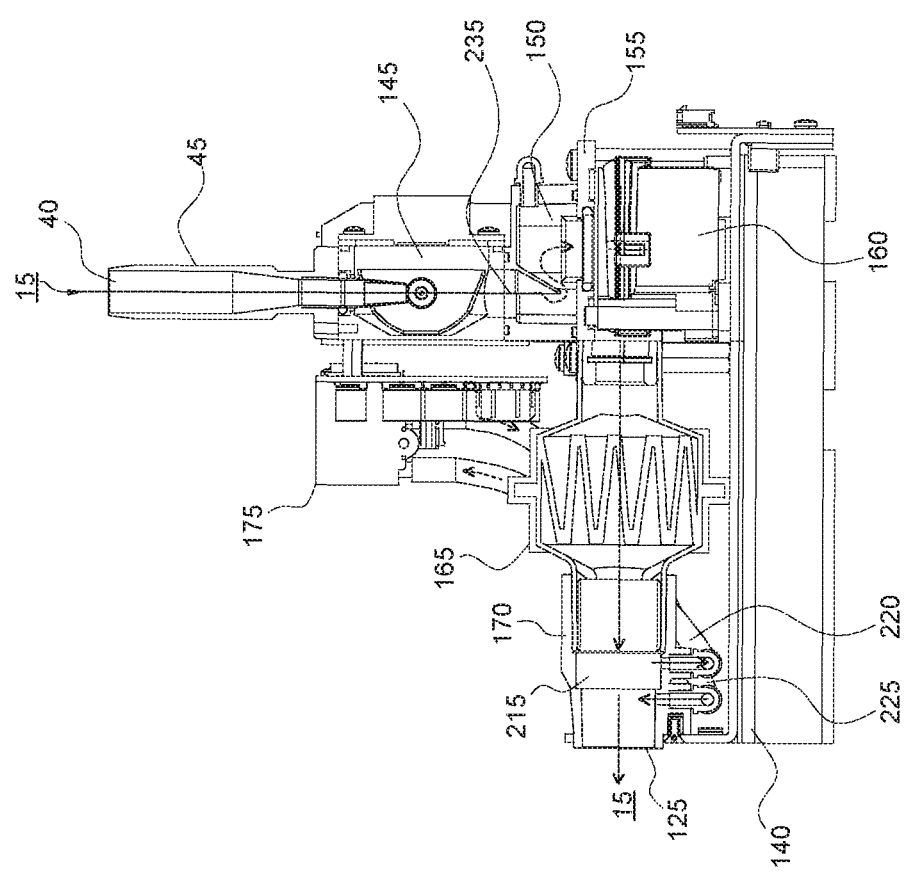
FIG. 4 is a sectional view of an internal portion of the particle counter of FIG. 1 along plane 4-4-4 in FIG. 3.
Figure 10:
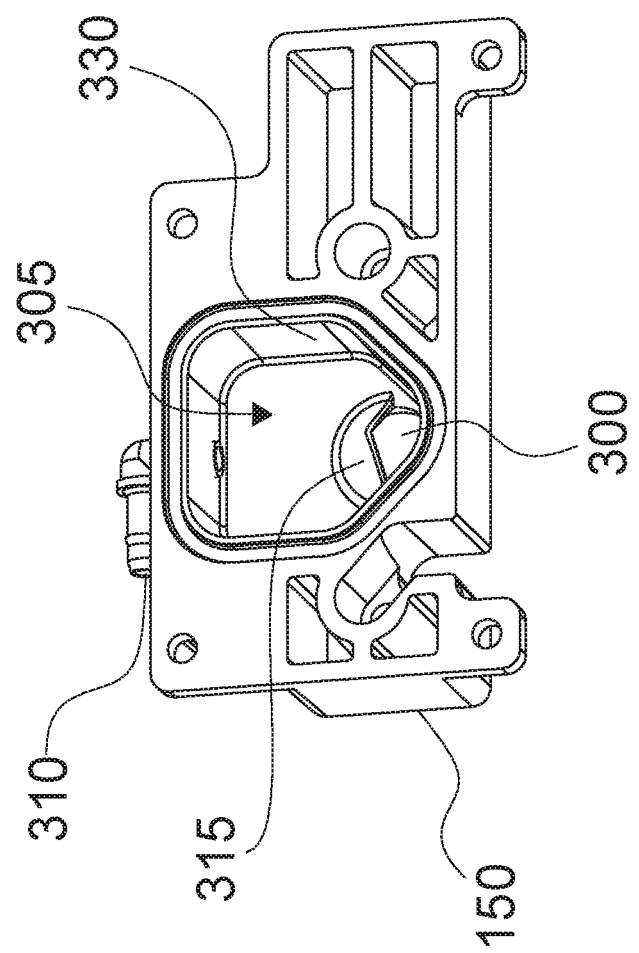
FIG. 10 is a perspective view of a flow connect block used in the particle counter of FIG. 1.

FIG. 10 shows a flow connect block 150 capable of being used with the invention. The flow connect block 150 includes a connector intake port 300, a connector exhaust port 305, and a connector vent port 310. The connector vent port 310 is coupled to the blower vent port 250 by a conduit 312 (FIG. 3). The connector intake port 300 includes a partial cone hood 315 to deflect liquid fluid that enters the flow path. The shown connector exhaust port 305 is plate shaped to encompass the port 300 and a through port 320 (best shown in FIG. 5) of the sensor/blower mounting plate 155. The through port 320 includes a lip 325 to limit liquid fluid from entering the blower 160. The liquid fluid can pool inside the chamber 330 and evaporate over time. The connector vent port 310 leads to the chamber 330, thereby allowing gaseous fluid to vent between the chamber 330 and the blower 160. The chamber 330 and the flow connect block 150 do not need to be as complex as shown. Rather, the flow connect block 150 can be a simpler flow connector. For example, the flow connector can be a simple conduit connecting the particle count sensor 145 to the blower 160 with the chamber being a simple tap for the connector vent port 310. It is also envisioned that the flow connector can be located elsewhere in the flow path. For example, it is envisioned that the flow connector can be after the blower exhaust port 245 and before the filter 165. Further, it is envisioned that the flow connect block 150 and the sensor/blower mounting plate 155 can be a unitary element. Further, it is envisioned that the blower could be enclosed.

Figure 16:
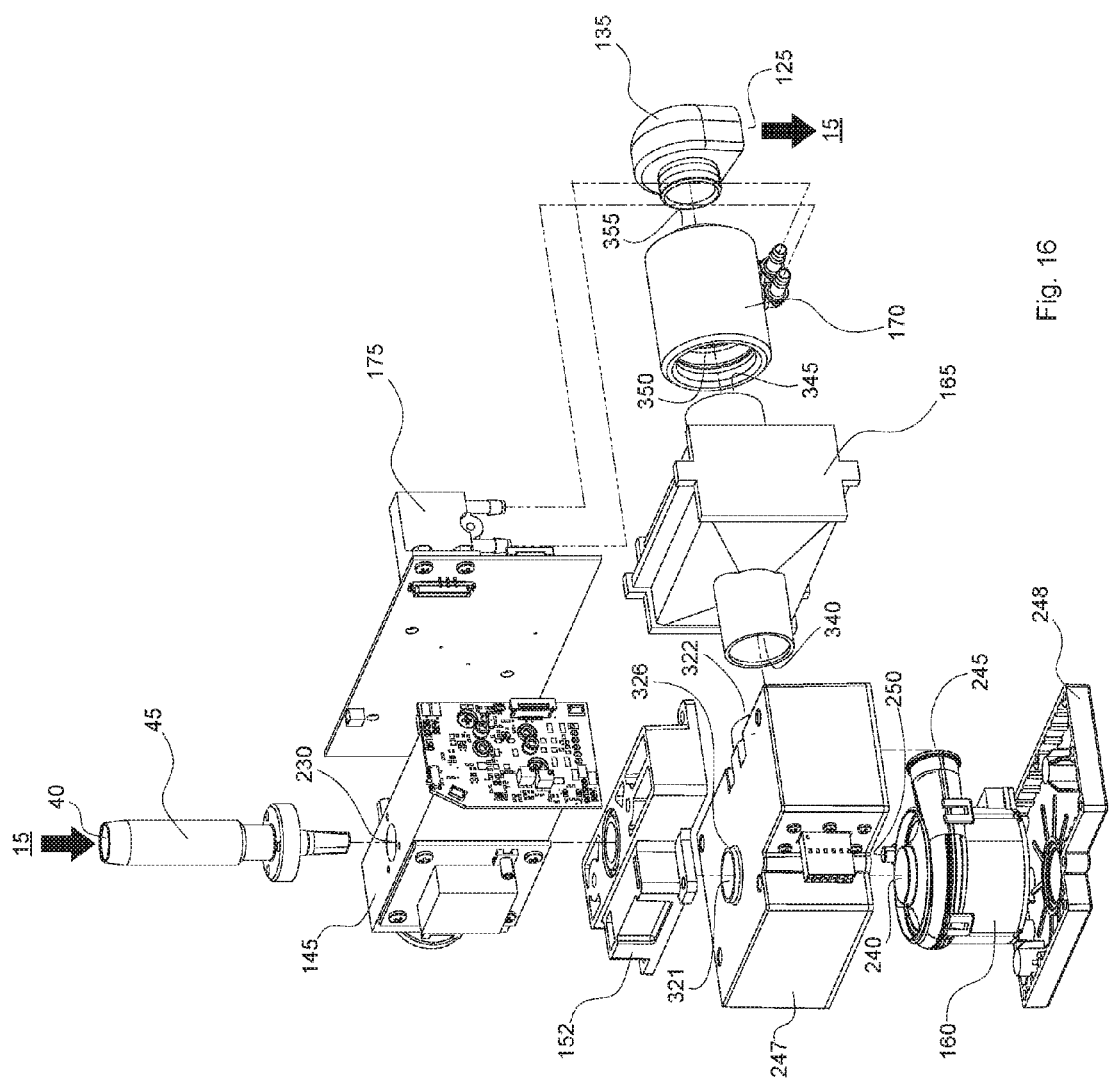
FIG. 16 is an exploded view of a portion of the gaseous-fluid flow system and fluid-flow path through the particle counter of FIG. 15.

For example, FIGS. 16 and 17 provide a second construction of the particle counter 10. As illustrated, rather than having the flow connect block 150 and the sensor/blower mounting plate 155, the second construction includes a riser block 152 and a sealed blower enclosure 246. The riser block 152 is similar to the flow connect block 150; however, the riser block 152 does not include the connector vent port 310. The sealed blower enclosure 246 includes a sealed blower box 247 and a sealed blower lid 248. The sealed blower enclosure 246 encapsulates the blower 160 such that the blower vent port 250 can draw or exhaust the gaseous fluid from or within the sealed blower enclosure 246. However, because the sealed blower enclosure 246 is sealed, the gaseous fluid cannot exhaust into the larger particle counter, and thereby, not avoid being filtered or counted. The sealed blower enclosure includes a through port 321 and lip 326 similar to the through port 320 and lip 326 of FIG. 5. The through ports 321 and 322 align with the blower intake port 240 and the blower exhaust port 245.

Referring again to FIGS. 3-6, the filter 165 filters particles in the gaseous fluid. The types of particles being filtered depend on the type and design of the filter 165. The filter includes a filter intake port 340 and a filter exhaust port 345. As already discussed, the location of the filter 165 in the flow path can be different from what is shown in the figures. The flow shunt 170, discussed earlier, includes a shunt intake port 350 and a shunt exhaust port 355.

Figure 5:
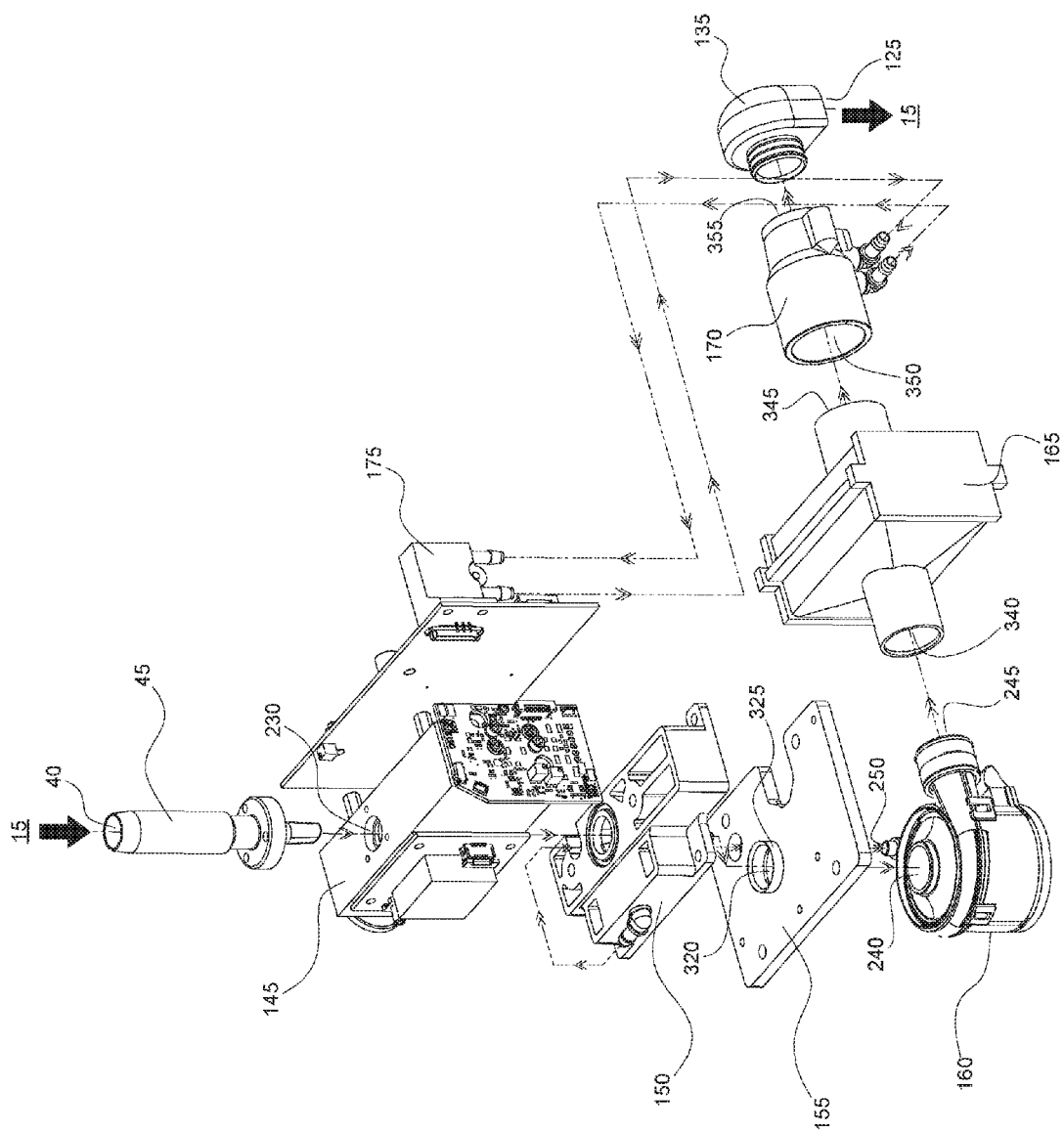
FIG. 5 is an exploded view of a portion of the gaseous-fluid flow system and fluid-flow path through the particle counter of FIG. 1.
Figure 6:
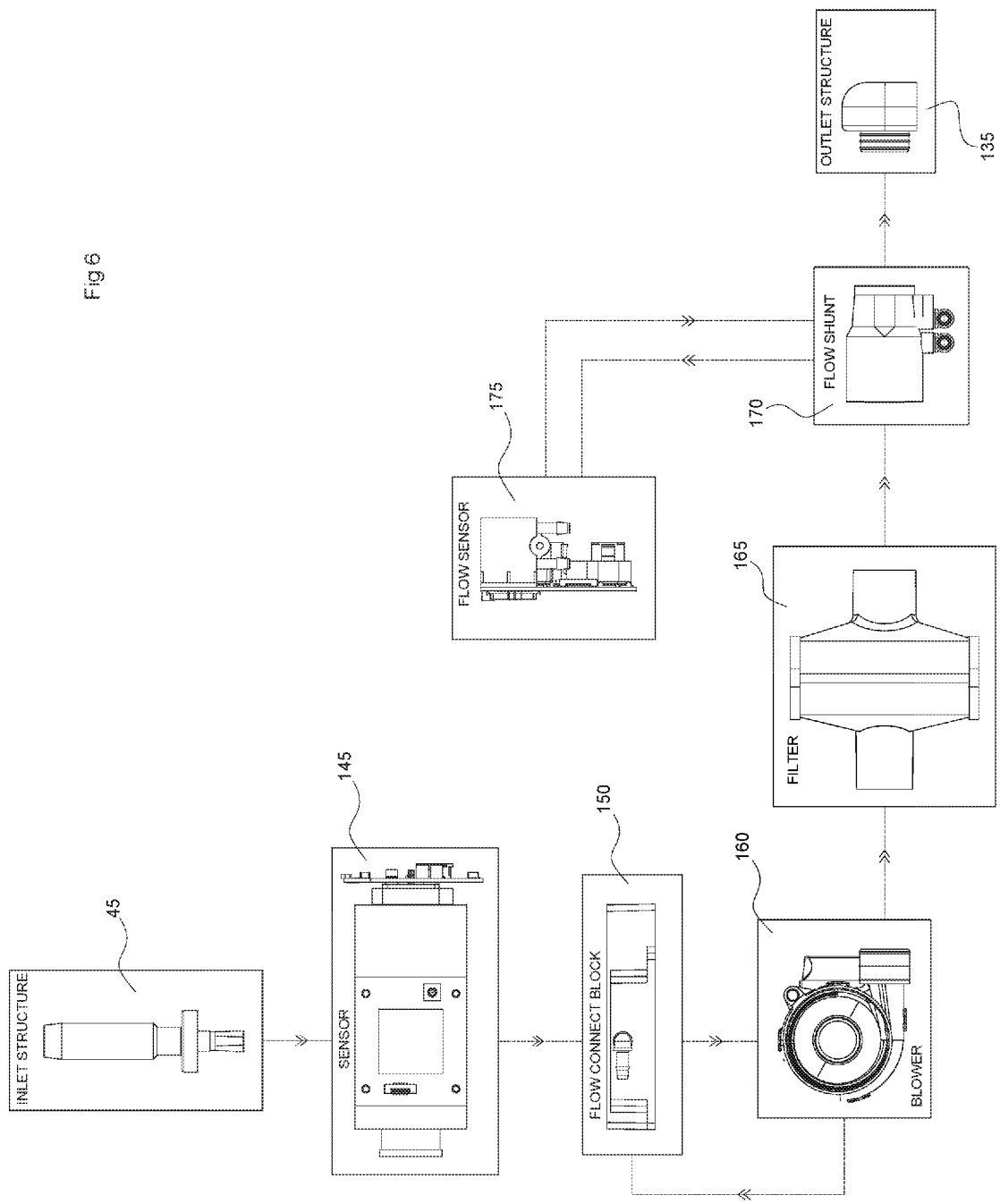
FIG. 6 is a block diagram representing a portion of the gaseous-fluid flow system fluid-flow path of FIG. 5.
Figure 7:
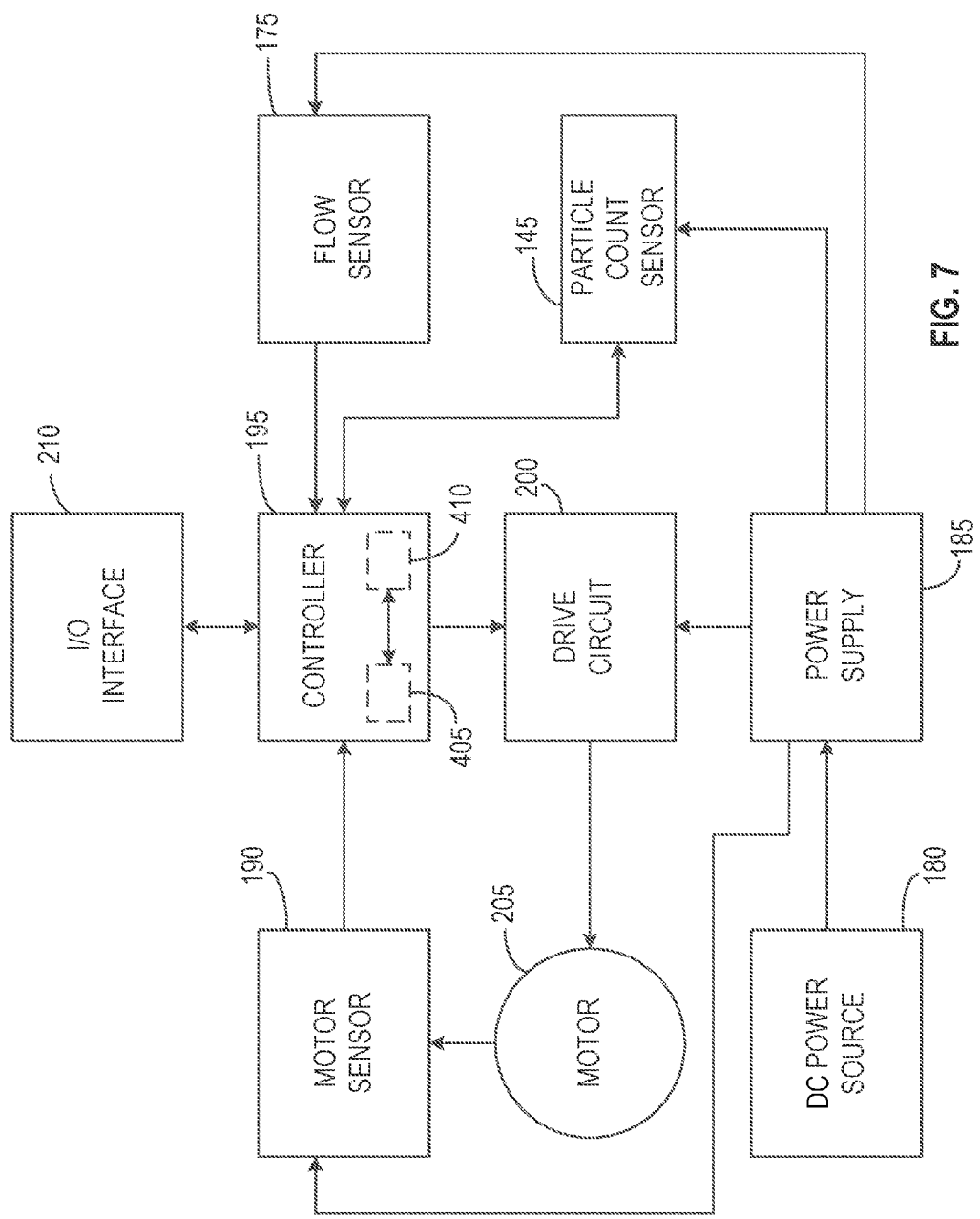
FIG. 7 is a block diagram representing a portion of the control system of the particle counter of FIG. 1.

With reference to FIGS. 5 and 7, the control system further includes multiple circuit boards 400. The circuit boards 400 are populated with a plurality of electrical and electronic components that provide power, operational control, and protection to the particle counter 10. The circuit boards 400 can support control elements (e.g., power supply 185, controller 195, communication input/output (I/O) interface 210, drive circuit 200, etc.) of the particle counter 10 or be coupled to control elements (e.g., motor 205, motor sensor 190, particle count sensor 145, flow sensor 175) of the particle counter 10. The circuit boards also include a plurality of additional passive and active components such as resistors, capacitors, inductors, integrated circuits, and amplifiers. These components are arranged and connected to provide a plurality of electrical functions to the circuit boards including, among other things, filtering, signal conditioning, or voltage regulation.

In some constructions, the controller 195 includes a processor 405 (e.g., a microprocessor, a digital signal processor, a microcontroller, or another suitable programmable device), a memory 410, and a bus. The bus connects various components of the PCB including the memory 410 to the processor 405. The memory 410 includes, for example, a read-only memory ("ROM"), a random access memory ("RAM"), a direct memory access (DMA) an electrically erasable programmable read-only memory ("EEPROM"), a flash memory, a hard disk, or another suitable magnetic, optical, physical, or electronic memory device. The processor 405 is connected to the memory 410 and executes firmware that is capable of being stored in the RAM (e.g., during execution), the ROM (e.g., on a generally permanent basis), or another non-transitory computer readable medium such as another memory or a disc. Additionally or alternatively, the memory 410 is included in the processor 405. It is also envisioned that the processor 405 can encompass multiple processors and the memory 410 can encompass multiple memories. The controller 195 also includes an input/output system for transferring data with other components (e.g., the communication I/O 210), receiving sensory signals (analog and/or digital) from other components (e.g., the motor sensor 190, the flow sensor 175, and the particle count sensor 145), and output control signals to other components (e.g., drive circuit 200). It is to be understood that the control system may be operable to perform other functions and operations not described herein.

In some constructions of the particle counter 10, the flow sensor 175 is a mass-flow sensor. Alternatively, a differential pressure transducer can be coupled to determine a parameter of the flow. A controller of the flow sensor 175 is operable to determine a parameter of the gaseous fluid and/or the gaseous-fluid flow through the particle counter 10 (e.g. mass, volume, speed, composition, etc.) based on information generated by the mass-flow sensor, the differential pressure transducer, or other input devices not specifically discussed herein.

In one example, the flow sensor 175 generates a signal indicative of the mass of gaseous fluid flowing through the particle counter 10 over a predetermined period of time. The signal generated by the flow sensor 175 can be supplied to the controller 195 to control the operation of the blower 160 and adjust the gaseous-fluid flow to a desired amount. In this particular example, it may be desired to maintain the gaseous-fluid flow at 100 liters per minute (LPM). The flow sensor 175 is operable to detect a variation of the gaseous-fluid flow to control the operation of the blower assembly and adjust the gaseous-fluid flow to 100 LPM. It is to be understood that this flow rate is only one example. Moreover, it is possible to operate the blower 160 to generate a variable flow rate over time through the particle counter 10 based on other information (e.g., temperature, humidity, particle count). It is envisioned that the sensor controller can be combined with the controller 195 such that the raw signal from the flow sensor 175 is provided to the controller 195.

The particle counter 10 can communicate with other devices via a wired or wireless connection through the communications I/O interface 210. The wireless communication can be via a wireless access point. The term "wired" is intended to define means of connection such as USB cable, DSL cable, Ethernet cable, and others. Similarly, the communication with the device can be over a network.

The power supply 185 supplies nominal voltages to the electrical and electronic components of the control system. The power supply 185 can be powered by mains power having nominal line voltages or a DC power source 180 (e.g., a battery). In one construction the power source 180 provides between 12 VDC and 24 VDC.

As discussed, the control system includes the controller 195, the drive circuit 200, the motor sensor 190, and the motor 205. Generally speaking, the controller 195 drives the motor 205 using the drive circuit 200 and based on sensed parameters. One example sensed parameter is rotor positioning determined through the motor sensor 190. Another parameter is the gaseous fluid flow through the particle counter 10. Further exemplary operations are discussed below.

Figure 11:
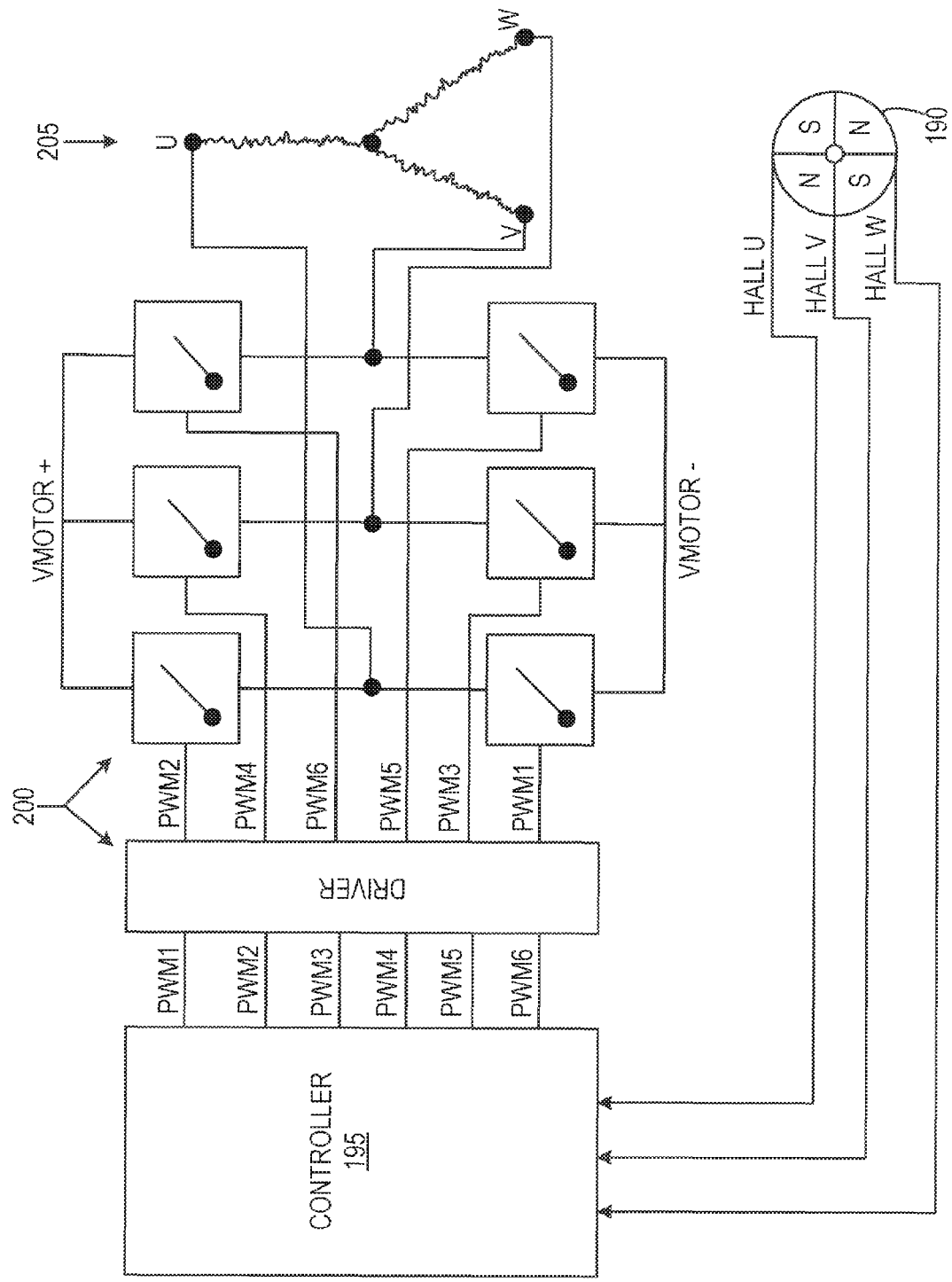
FIG. 11 is a schematic diagram representing a control circuit for a 3-phase brushless direct current motor.

One example motor discussed above that is capable of being used with the particle counter 10 is a brushless direct current (BLDC) motor. More specifically, the motor can be a 3-phase, 8-pole BLDC motor with Hall-Effect sensing. A representative circuit for controlling this type of motor is shown in FIG. 11. The power supply 185 provides a high bus voltage and a low bus voltage to an inverter consisting of six switches. The six switches are arranged in a bridge circuit forming an inverter. The controller 195 issues drive signals (PWM1 through PWM6) to control the six switches. The switches can power electronic field-effect transistors driven directly by the controller 195 or through a driver, as shown. The switches vary the flow of current to the motor 205. Hall-Effect sensors are used to generate signals having a relation to the rotational position of the motor's rotor. The signals are provided to the controller 195. Other methods of determining rotational positioning (e.g., back EMF) can be used.

One example commutation sequence involves a six step commutation sequence. The following PWM drive signals can be utilized for a six step sequence.

TABLE 1

| STATE | ACTIVE PWMs |
| --- | --- |
| 1 | PWM4, PWM5 |
| 2 | PWM2, PWM5 |
| 3 | PWM2, PWM3 |
| 4 | PWM6, PWM3 |
| 5 | PWM6, PWM1 |
| 6 | PWM4, PWM1 |

Before proceeding further, one skilled in the art would understand that the basic PWM sequence discussed herein can be further refined by providing more complex pulse shapes, including the shape being trapezoidal or stepped, and more complex sequencing.

In one implementation, the particle counter 10 includes multiple operation states, referred to herein as "NORMAL," "SKIP," and "BRAKE." The provided names are exemplary and different names can be used to refer to the three states discussed herein. The operation state refers to, in part, how the basic commutation sequence is further refined, if at all. For example, the operation state referred to as NORMAL is a state that controls the switches in a conventional step sequence. For a further example, NORMAL can proceed through the six commutation states as shown in Table 1, above.

A second operation state is referred to as SKIP. For SKIP, less than all of the available commutation states are used for commutating the motor 205. For a more specific example, the first, third, and fifth commutation pulses or the second, fourth, and sixth commutation states are used for commutating the motor 205. The rotor coasts through the non-excited commutation pulses. This allows the stator to push (or pull) the rotor based on the excited pulses.

A third operation state is referred to as BRAKE. For BRAKE, at least one of the commutation pulses is commutated in an opposite sequence of the normal commutation sequence, thereby providing an electronic brake to the motor 205 for the braking pulse. The BRAKE sequence can include multiple pulses in the opposite direction, although the electronics of the motor 205 needs to be designed to allow for additional energy surges originating from the electromagnetics of the motor 205. Also, the BRAKE sequence can be superimposed on a SKIP commutation sequence. For example, the first and third commutation pulses can commutate as shown in Table 1, while the second, fourth, and sixth pulses are skipped, and the fifth commutation pulse is reversed to allow for the electronic brake. In some environments, under some scenarios, simply pushing the air doesn't adequately slow the rotor. So an electronic drag is temporarily applied to slow down the motor.

Figure 12:
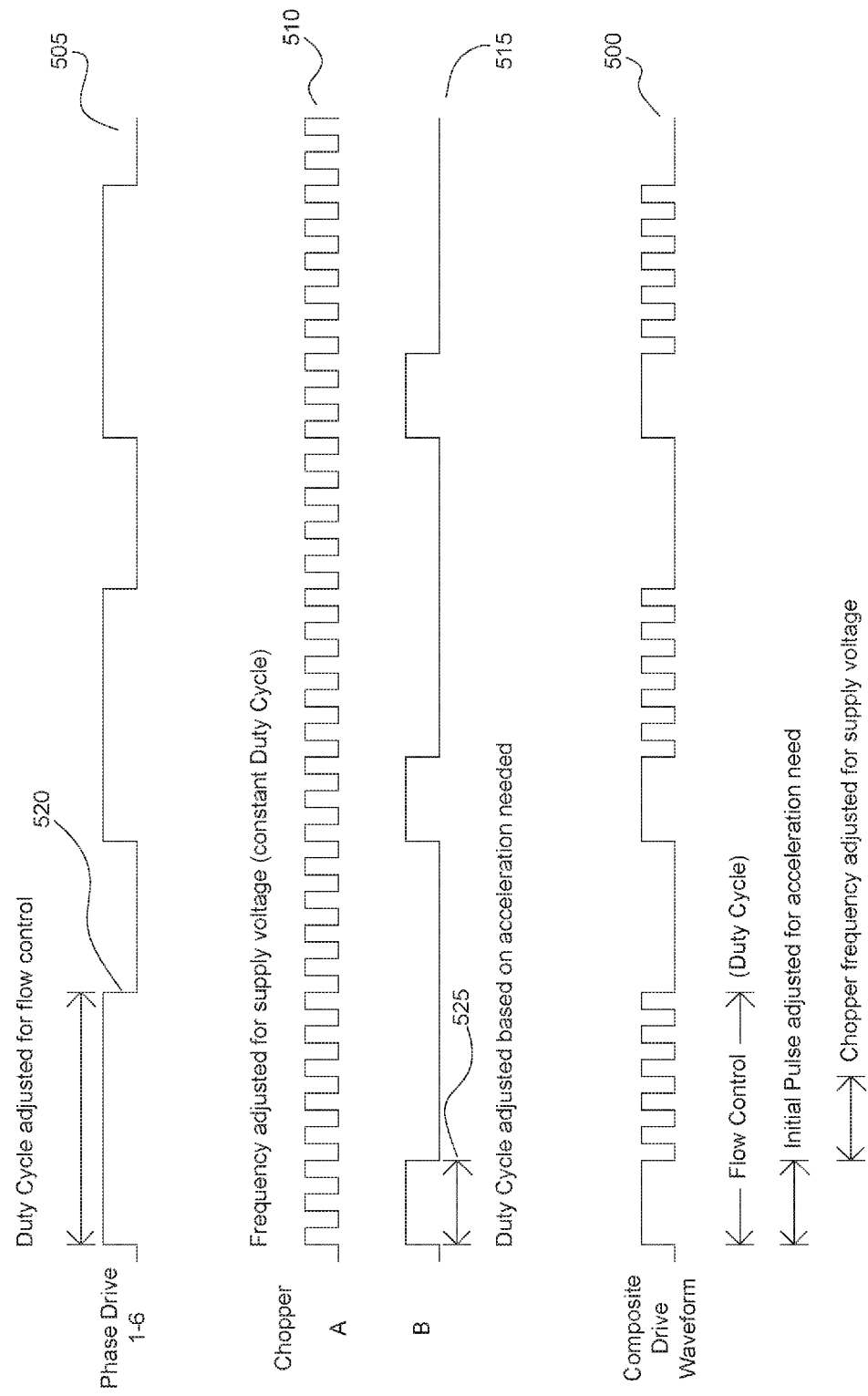
FIG. 12 provide representative component and composite waveforms for providing a motor drive waveform.

In addition to the commutation state, the motor drive waveform can be constructed to accommodate advantages of the fluid dynamic bearing motor 205. The motor drive waveform can be a composite drive waveform of multiple component waveforms. For example, one composite drive waveform 500 is shown in FIG. 12. The composite drive waveform 500 consists of three component waveforms 505, 510, and 515. The composite drive waveform 500, in one implementation, provides the commutation phases discussed earlier. The first component waveform 505 is a duty cycle adjusted pulse. The duty cycle value 520 can be adjusted for flow control, similar to what was been described in the earlier incorporated patent documents. For example, if the amount of energy needs to increase for increasing flow, then the duty cycle for the pulse can be increased. Similarly, if the amount of energy needs to decrease for decreasing flow, then the duty cycle for the pulse can be decreased. The type of control used for the first component can be one of many known types including, proportional control, proportional-derivative control, proportional-integral-derivative control, and other known control schemes.

The second component waveform 510 is a frequency adjusted waveform that is adjusted based on the supply voltage. In some implementations, the particle counter 10 can be battery powered (e.g., by the DC power source 180 of FIG. 7). The frequency adjusted waveform is frequency adjusted for the varying supply voltage. For example, one maximum battery powered supply voltage may be 24 VDC. Through usage, the supply voltage starts to decrease and may result in the particle counter 10 having a supply voltage range of 12 VDC to 24 VDC. This means that without performing voltage boosting, the voltage difference between the high voltage bus and the low voltage bus will be substantially analogous to the supply voltage range of 12V to 24V. The frequency adjusted waveform provides further energy control for the electronic commutation as the supply voltage decreases. The supply voltage may be monitored either at the battery or at the bus voltage for the drive. The frequency adjusted waveform has a higher frequency with a greater supply voltage and has a lower frequency for a lower supply voltage. Again, the type of control used for the second component can be one of many known types including, proportional control, proportional-derivative control, proportional-integral-derivative control, and other known control schemes.

The third component waveform 515 is a duty cycle adjusted waveform that is adjusted based on a necessary initial rotational acceleration. The frequency adjusted waveform provides benefit for the varying supply voltage of the particle counter 10. The duty cycle adjusted waveform 515 provides an initial energy burst to push/pull the rotor to the next commutation sequence while the frequency adjusted waveform 510 helps to maintain the energy delivered during the remaining duty cycle adjusted for flow control 520 by compensating for the supply voltage. The duty cycle 525 is adjusted based on the burst or acceleration needed to rotate to the next commutation pulse. A side effect of the frequency adjusted waveform is that it brings down the total energy delivered with the waveform. The initial pulse accelerates the rotor independently of supply voltage, and the chopper frequency helps compensate for changes in acceleration that would occur due to the varying supply voltage.

The composite drive waveform 500 is the combination of all three component waveforms. More specifically, the frequency adjusted waveform 510 and the duty cycle adjusted waveform 515 can result from an OR operation. The result of the OR operation can be combined with the duty cycle adjusted waveform 505 through an AND operation. The OR and AND operations can be performed in software and/or hardware. The resulting composite drive waveform 500 is shown in FIG. 12.

Before proceeding further, other composite waveforms are possible. For example, the shown waveforms are shown as square waveforms. However, one or more of the waveforms can be more complex. For a more specific example, the duty cycle adjusted waveform 505 can be a trapezoidal or stepped waveform to improve transitioning and cogging with the BLDC motor. Also, it is envisioned that not all three of the component waveforms are required in all operations. For example, rather than providing a BRAKE operation as discussed earlier, the BRAKE operation can be accomplished through the removal of the duty cycle adjusted waveform 515 and performing an AND operation with only the duty cycle adjusted waveform 505 and the frequency adjusted waveform 510.

Figure 13A:
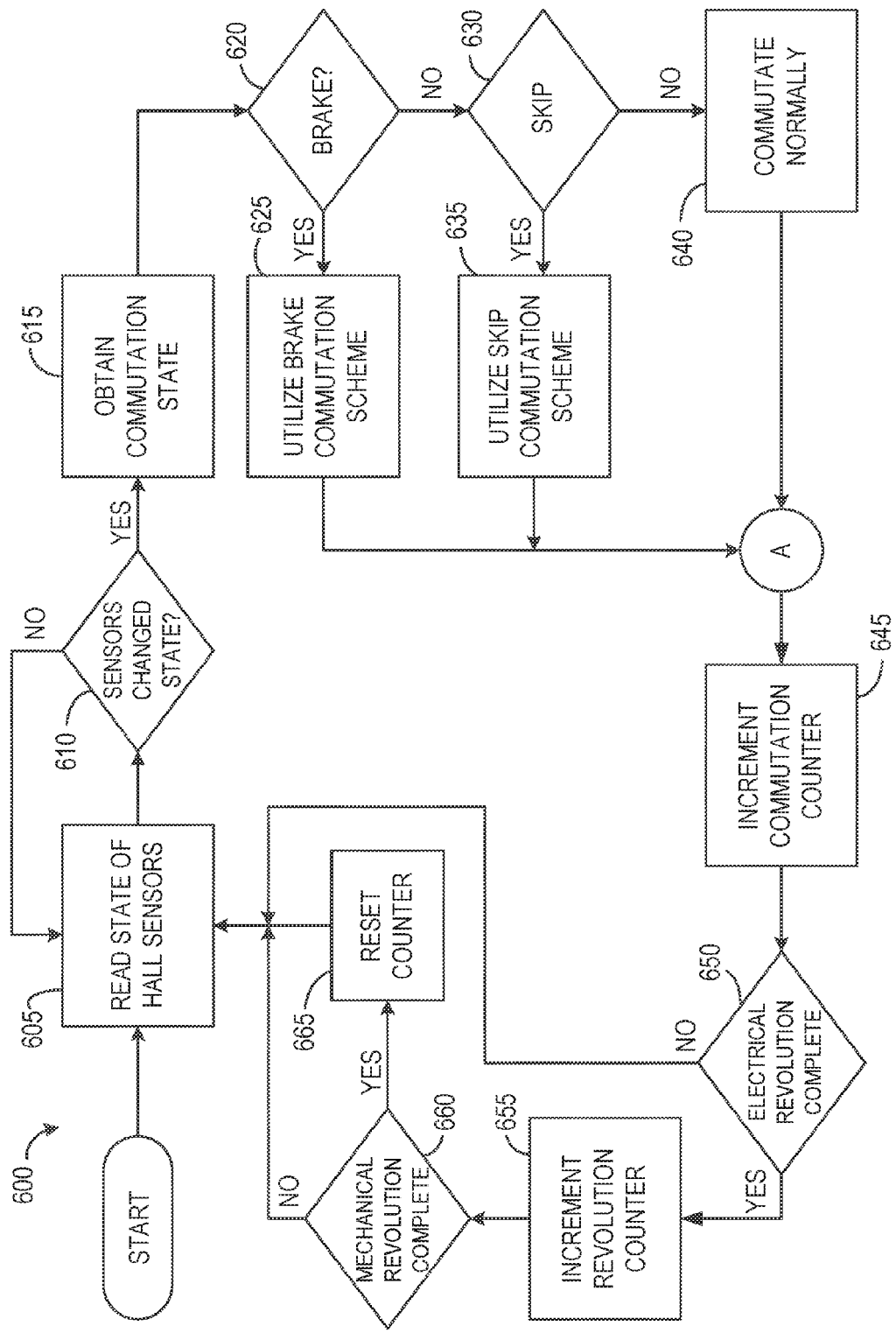
FIGS. 13A and 13B are flow charts for an operational flow for the particle counter.
Figure 13B:
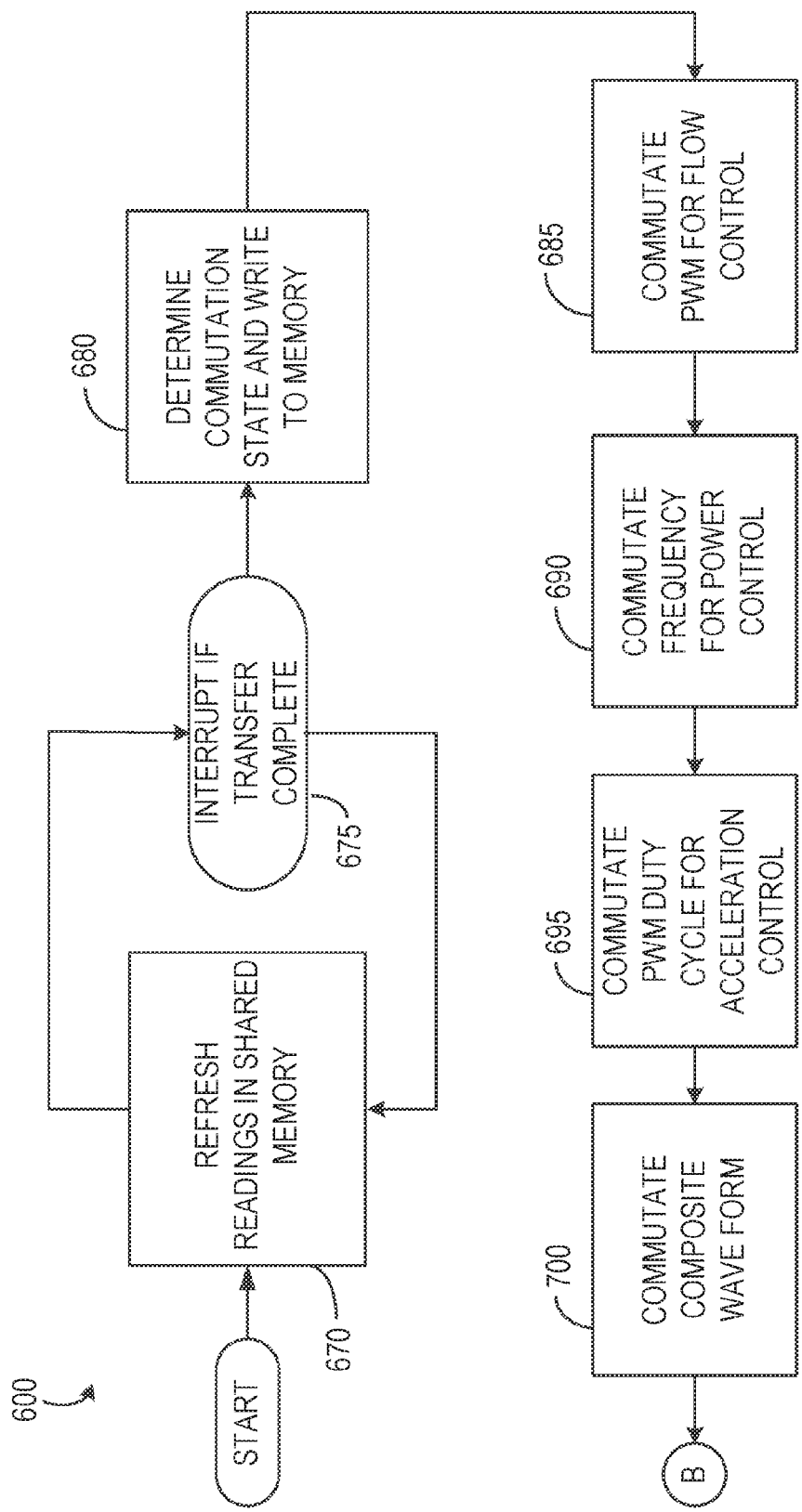

FIGS. 13A and 13B provide an operational flow for the particle counter 10. Upon receiving power, the controller 195 performs a standard initialization, including the configuration of registers, clocks, and peripherals. One exemplary construction of the controller 195 includes a direct memory access (DMA) storage. The DMA storage allows for storage of data (e.g., parameters and states) that can be shared among multiple processors in the controller 195. This allows for the multiple processes shown in FIGS. 13A and 13B. Alternatively, a single processor can perform the processes shown in FIGS. 13A and 13B.

The process 600 shown in FIG. 13A can be accomplished by a first processor and controls commutation. The process 601 shown in FIG. 13B can be accomplished by a second processor and develops the composite waveform, among other actions. The processes in FIGS. 12A and 12B assume the motor 205 has already started and is rotating. A start routine as known in the art can be used to initiate movement of the motor 205.

At block 605, the first processor reads the state of the hall sensors 190 and determines whether the hall sensors 190 have changed state (block 610). The changing of the state of the hall sensors 190 indicate the rotor has rotated the necessary number of degrees to a next rotor position for applying a possible next commutation pulse to the stator windings.

At block 615, the first processor obtains the commutation state from the shared memory. The commutation state is decided as part of the process 601, discussed below, and saved in a shared memory location.

At block 620, the first processor determines whether a BRAKE state was recalled from the shared memory. If yes, then the first processor utilizes a Brake commutation scheme (block 625).

At block 630, the first processor determines whether a SKIP state was recalled from the DMA memory. If yes, then the first processor utilizes a SKIP commutation scheme (block 635).

If NORMAL state was recalled, then the first processor provides a NORMAL commutation scheme (block 640).

Whether a commutation pulse is generated depends on the state and the location of the rotor within the commutation sequence. For example, the commutation pulse may be a normal pulse (in NORMAL), no pulse (in SKIP), or a brake pulse (in BRAKE).

At block 645, the first processor increments the commutation counter from one to six, depending on the current state of the commutation counter. This provides sequence control for the commutation sequence.

At block 650, the first processor determines if a revolution of the commutation sequence is complete. If yes, a revolution counter is incremented (block 655); otherwise the process proceeds to block 605. While six commutations are used per electrical revolution, the stator may include more commutations steps per physical revolution. For example, an eight pole rotor may utilize twenty four commutation steps per physical revolution. The revolutions counter helps to identify the physical location of the rotor. If the mechanical revolution is complete (block 660), then the revolution counter resets (block 665).

For the process 601 shown in FIG. 13B, a second processor refreshes readings (block 670) in the shared memory for flow, drive voltage, temperature, drive current, and other control inputs. Upon completion, an interrupt (block 675) is generated alerting the second processor to proceed to block 680. Starting with block 680, the second processor determines whether the operational state should be BRAKE, SKIP, or NORMAL, and writes the state to the shared memory. The second processor then calculates the PWM duty cycle for flow control (block 685), calculates the frequency for power conserve control (block 690), and calculates the PWM duty cycle for acceleration control (block 695). The construction of these component waveforms 505, 510, and 515 can be determined as discussed above. The second processor then constructs (block 700) the composite drive waveform 500 using the component waveforms 505, 510, and 515.

With the composite waveform (ref. B in FIG. 13B), the commutation counter, and the commutation state (ref. A in FIG. 13A), the controller 195 controls the driver 200 to drive the motor, and consequently the impeller. The hall sensors 190 detect the movement of the rotor and the processes of FIGS. 13A and 13B repeat.

Figure 14:
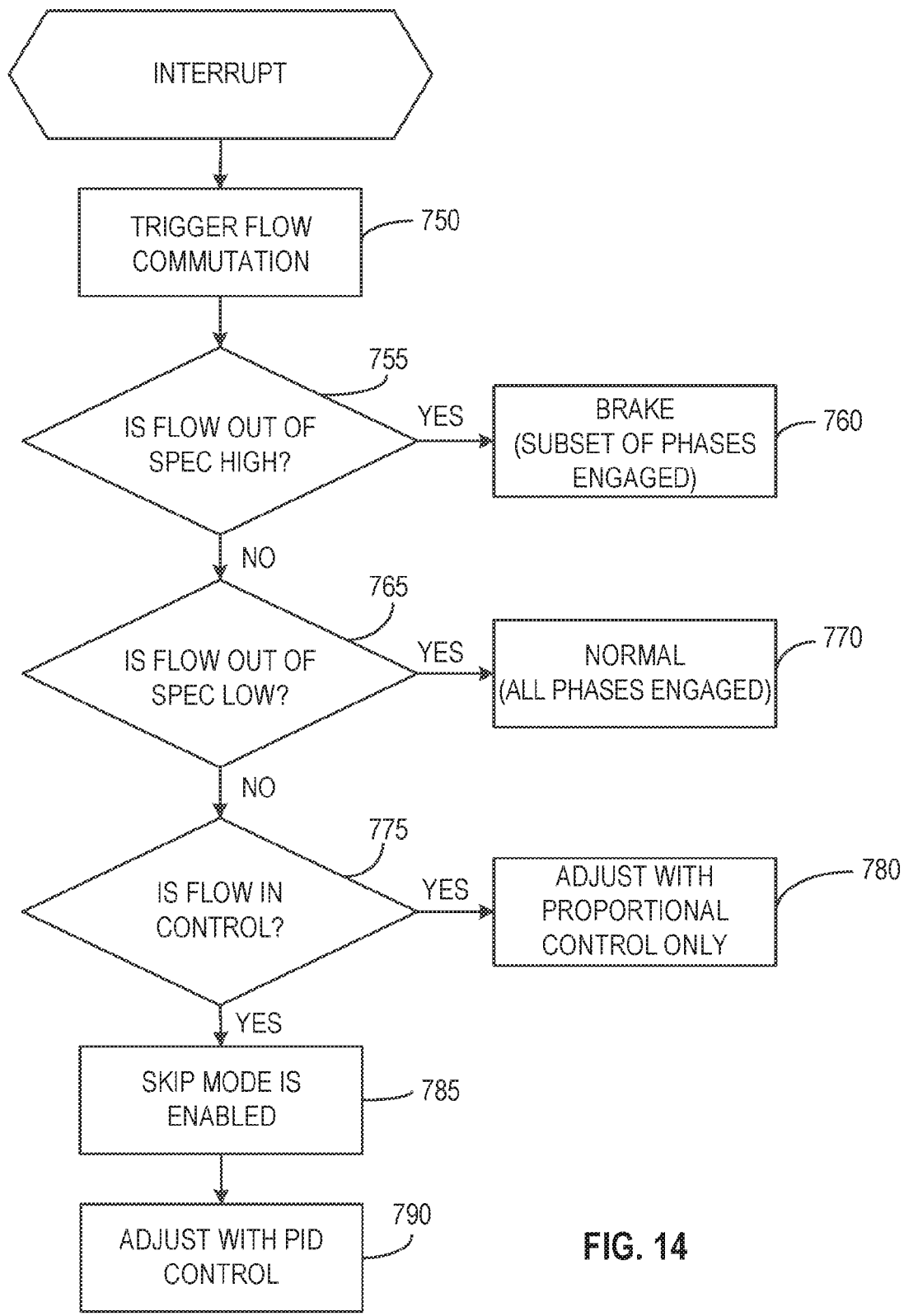
FIG. 14 is a flow chart of a decision tree for a commutation state.
Figure 15:
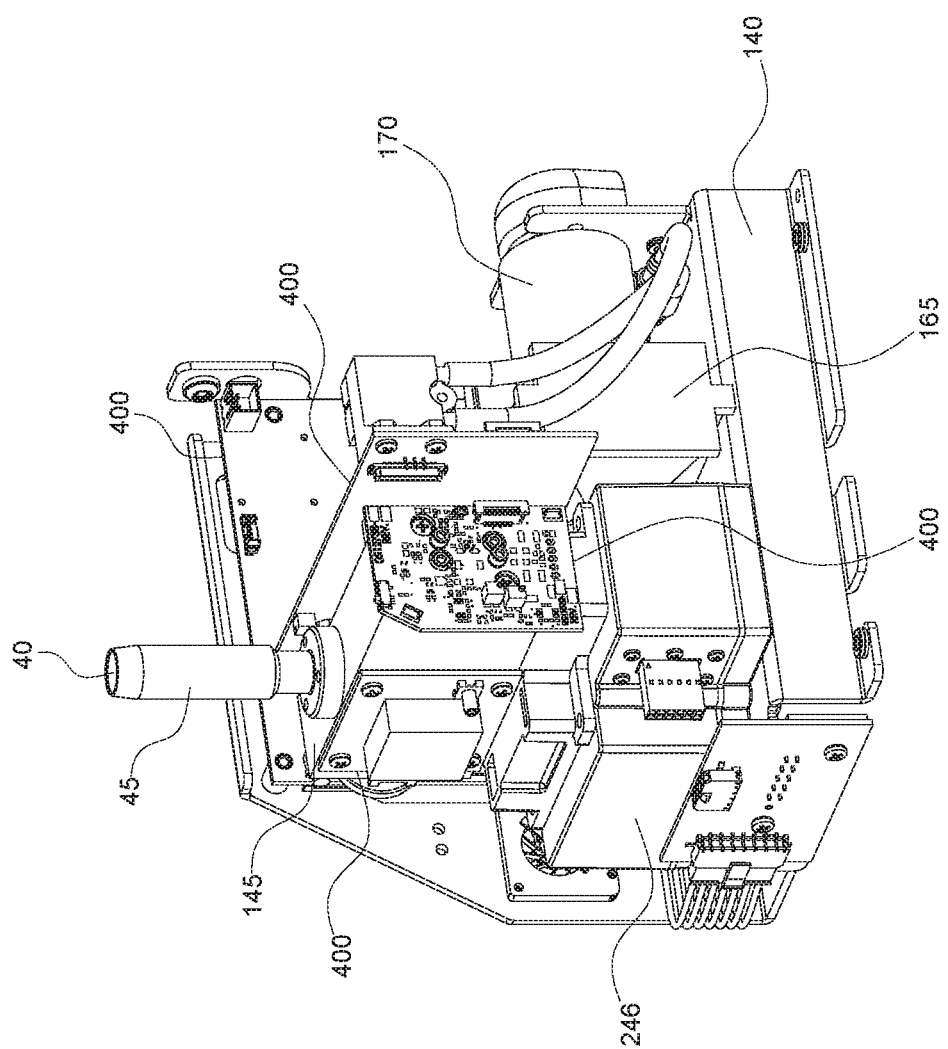
FIG. 15 is a perspective view of an internal portion of a second particle counter.

An exemplary decision tree for blocks 680 and 685 is provided in FIG. 14. For block 750, a flow value for the particle counter is calculated with parameters provided by the flow sensor 175. Alternatively, the flow sensor may include a processor for providing the flow calculation. If the flow is high and out of specification (block 755), then the BRAKE state is recorded in shared memory. If the flow is low and out of specification (block 765), then a NORMAL state (block 770) is recorded in shared memory and the PWM control for the duty cycle adjusted for flow control (component waveform 505) is set to a maximum duty cycle. If the flow is in specification but not in control (block 775), then the NORMAL state is recorded and the duty cycle for flow control is adjusted with proportional control (block 780). If the flow is in specification and in control, then the SKIP mode is enabled (block 785). Also, the duty cycle for flow control is constructed with a proportional-integrated-derivative control scheme (block 790).

Accordingly, the invention provides a new and useful environmental sensor and method of operating the same. Various features and advantages of the invention are set forth in the following claims.

What is claimed is:

1. A gaseous-fluid environmental sensor, comprising:
a gaseous-fluid flow system defining a flow path coupling an intake port to an exhaust port, the gaseous-fluid flow system including a blower and a flow sensor, the blower including a motor and the flow sensor sensing a flow-related parameter, wherein the motor includes a motor having a fluid dynamic bearing;
a battery;
an electrical sensor sensing an electrical power-related parameter;
a controller electrically coupled to the electrical sensor, the flow sensor, and the motor, the controller being configured to generate a composite drive waveform having a first component based on the sensed flow-related parameter and a second component based on the sensed electrical power-related parameter, the controller being further configured to drive the motor using the composite drive waveform.

2. The gaseous-fluid environmental sensor of claim 1, wherein the electrical power-related parameter includes a sensed battery voltage.

3. The gaseous-fluid environmental sensor of claim 1, wherein the electrical power-related parameter includes a sensed motor voltage.

4. The gaseous-fluid environmental sensor of claim 1, wherein the sensed flow-related parameter includes a sensed mass of gaseous fluid flow through the gaseous-fluid environmental sensor.

5. A gaseous-fluid environmental sensor, comprising:
a gaseous-fluid flow system defining a flow path coupling an intake port to an exhaust port, the gaseous-fluid flow system including a blower and a flow sensor, the blower including a motor and the flow sensor sensing a flow-related parameter;
a battery;
an electrical sensor sensing an electrical power-related parameter;
a controller electrically coupled to the electrical sensor, the flow sensor, and the motor, the controller being configured to generate a composite drive waveform having a first component based on the sensed flow-related parameter and a second component based on the sensed electrical power-related parameter, the controller being further configured to drive the motor using the composite drive waveform;
wherein the second component includes a frequency adjusted waveform having a frequency that varies based on the sensed electrical power-related parameter.

6. A gaseous-fluid environmental sensor, comprising:
a gaseous-fluid flow system defining a flow path coupling an intake port to an exhaust port, the gaseous-fluid flow system including a blower and a flow sensor, the blower including a motor and the flow sensor sensing a flow-related parameter;
a battery;
an electrical sensor sensing an electrical power-related parameter;
a controller electrically coupled to the electrical sensor, the flow sensor, and the motor, the controller being configured to generate a composite drive waveform having a first component based on the sensed flow-related parameter and a second component based on the sensed electrical power-related parameter, the controller being further configured to drive the motor using the composite drive waveform; and wherein the second component includes a pulse width modulated waveform having a pulse width that varies based on the sensed flow-related parameter.

7. A gaseous-fluid environmental sensor, comprising:
a gaseous-fluid flow system defining a flow path coupling an intake port to an exhaust port, the gaseous-fluid flow system including a blower and a flow sensor, the blower including a motor and the flow sensor sensing a flow-related parameter;
a battery;
an electrical sensor sensing an electrical power-related parameter;
a controller electrically coupled to the electrical sensor, the flow sensor, and the motor, the controller being configured to generate a composite drive waveform having a first component based on the sensed flow-related parameter and a second component based on the sensed electrical power-related parameter, the controller being further configured to drive the motor using the composite drive waveform;
wherein the composite drive waveform further has a third component based on a desired rotational burst.

8. The gaseous-fluid environmental sensor of claim 7, wherein the third component includes a pulse width modulated waveform having a pulse width that varies based on the second component.

9. A gaseous-fluid environmental sensor, comprising:
a gaseous-fluid flow system defining a flow path coupling an intake port to an exhaust port, the gaseous-fluid flow system including a blower and a flow sensor, the blower including a motor and the flow sensor sensing a flow-related parameter;
a battery;
an electrical sensor sensing an electrical power-related parameter;
a controller electrically coupled to the electrical sensor, the flow sensor, and the motor, the controller being configured to generate a composite drive waveform having a first component based on the sensed flow-related parameter and a second component based on the sensed electrical power-related parameter, the controller being further configured to drive the motor using the composite drive waveform;
wherein the motor is a high revolutions per minute (RPM) motor operable up to between 20,000 and 40,000 RPM, and
wherein the blower further includes a rotor/impeller assembly, wherein the motor includes a rotor of the rotor/impeller assembly, and wherein the rotor/impeller assembly has a mass between 25 and 45 grams.

10. A method of controlling a gaseous-fluid environmental sensor, the method comprising;
creating a flow of fluid from a space through the gaseous-fluid environmental sensor;
determining a flow-related parameter of the flow of fluid;
determining an electrical power-related parameter of the gaseous-fluid environmental sensor;
generating a first component of a composite drive waveform based on the determined flow-related parameter;
generating a second component of the composite drive waveform based on the determined electrical power-related parameter; and
driving a motor with the composite drive waveform;
wherein driving the motor includes driving the motor with a commutation sequence having a plurality of steps, and wherein each step includes the composite drive waveform.

11. The method of claim 10, wherein the determining the electrical power-related parameter includes sensing a parameter related to a battery voltage.

12. The method of claim 10, wherein the determining the electrical power-related parameter includes sensing a parameter related to a motor voltage.

13. The method of claim 10, wherein the determining the flow-related parameter includes sensing a mass of gaseous fluid flow through the gaseous-fluid environmental sensor.

14. A method of controlling a gaseous-fluid environmental sensor, the method comprising;
creating a flow of fluid from a space through the gaseous-fluid environmental sensor;
determining a flow-related parameter of the flow of fluid;
determining an electrical power-related parameter of the gaseous-fluid environmental sensor;
generating a first component of a composite drive waveform based on the determined flow-related parameter;
generating a second component of the composite drive waveform based on the determined electrical power-related parameter; and
driving a motor with the composite drive waveform;
wherein the generating the first component of the composite drive waveform includes generating a frequency adjusted waveform having a frequency that varies based on the determined electrical power-related parameter.

15. A method of controlling a gaseous-fluid environmental sensor, the method comprising;
creating a flow of fluid from a space through the gaseous-fluid environmental sensor;
determining a flow-related parameter of the flow of fluid;
determining an electrical power-related parameter of the gaseous-fluid environmental sensor;
generating a first component of a composite drive waveform based on the determined flow-related parameter;
generating a second component of the composite drive waveform based on the determined electrical power-related parameter; and
driving a motor with the composite drive waveform;
wherein the generating a second component of the composite drive waveform includes generating a pulse width modulated waveform having a pulse width that varies based on the determined flow-related parameter.

16. A method of controlling a gaseous-fluid environmental sensor, the method comprising;
creating a flow of fluid from a space through the gaseous-fluid environmental sensor;
determining a flow-related parameter of the flow of fluid;
determining an electrical power-related parameter of the gaseous-fluid environmental sensor;
generating a first component of a composite drive waveform based on the determined flow-related parameter;
generating a second component of the composite drive waveform based on the determined electrical power-related parameter; and
driving a motor with the composite drive waveform;
further comprising generating a third component of the composite drive waveform based on a desired rotational burst.

17. The method of claim 16, wherein the generating the third component of the composite drive waveform includes generating a pulse width modulated waveform having a pulse width that varies based on the second component.

* * * * *